US012385929B2

(12) United States Patent
Joyce et al.

(10) Patent No.: US 12,385,929 B2
(45) Date of Patent: *Aug. 12, 2025

(54) SYSTEMS AND METHODS FOR A COMBINED STRIP DETECTION AND HEATING SYSTEM IN AN ELECTROCHEMICAL TEST STRIP

(71) Applicant: POLYMER TECHNOLOGY SYSTEMS, INC., Whitestown, IN (US)

(72) Inventors: Joseph P. Joyce, Lafayette, IN (US); Gary Grubbs, Whitestown, IN (US); Christopher A. Dailey, Whitestown, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 624 days.

This patent is subject to a terminal disclaimer.

(21) Appl. No.: 16/701,053

(22) Filed: Dec. 2, 2019

(65) Prior Publication Data

US 2020/0174025 A1   Jun. 4, 2020

Related U.S. Application Data

(60) Provisional application No. 62/774,288, filed on Dec. 2, 2018.

(51) Int. Cl.
*G01N 33/72* (2006.01)
*G01N 1/44* (2006.01)
(Continued)

(52) U.S. Cl.
CPC ............. *G01N 33/723* (2013.01); *G01N 1/44* (2013.01); *G01N 27/3272* (2013.01);
(Continued)

(58) Field of Classification Search
CPC .... G01N 33/723; G01N 1/44; G01N 27/3272; G01N 33/4915; G01N 2333/805;
(Continued)

(56) References Cited

U.S. PATENT DOCUMENTS

2002/0122747 A1* 9/2002 Zhao ................. B01L 3/502707
204/601
2003/0079987 A1  5/2003 Hodges et al.
(Continued)

FOREIGN PATENT DOCUMENTS

CN   105849541 A   8/2016
CN   106922126 A   7/2017
(Continued)

OTHER PUBLICATIONS

International Search Report and Written Opinion dated Feb. 18, 2020 issued in related PCT App. No. PCT/US2019/064062 (14 pages).

(Continued)

*Primary Examiner* — Elizabeth A Robinson
*Assistant Examiner* — Sophia Y Lyle
(74) *Attorney, Agent, or Firm* — Haynes and Boone, LLP

(57) ABSTRACT

A system for testing for an analyte includes a test strip. The test strip includes a test strip detection conductor. The test strip includes a first flow path, the first flow path including a heating area, the test strip detection conductor in the heating area, the test strip detection conductor configured to be activated to heat a sample in the heating area.

15 Claims, 4 Drawing Sheets

(51) Int. Cl.
    *G01N 27/327*     (2006.01)
    *G01N 33/49*     (2006.01)
    *H01B 1/02*     (2006.01)
    *B01L 3/00*     (2006.01)

(52) U.S. Cl.
    CPC ........... *G01N 33/4915* (2013.01); *H01B 1/02* (2013.01); *B01L 3/502* (2013.01); *B01L 2300/0825* (2013.01); *B01L 2300/18* (2013.01); *B01L 2400/00* (2013.01); *G01N 2333/805* (2013.01)

(58) Field of Classification Search
    CPC .... G01N 33/726; G01N 27/26; G01N 1/4044; H01B 1/02; B01L 3/502; B01L 2300/0825; B01L 2300/18; B01L 2400/00; B01L 2300/0645; B01L 2300/0816; B01L 2300/0887; B01L 2300/1827; B01L 2400/0406; B01L 3/5027
    See application file for complete search history.

(56) References Cited

U.S. PATENT DOCUMENTS

| | | |
|---|---|---|
| 2006/0194331 A1 | 8/2006 | Pamula et al. |
| 2011/0302778 A1 | 12/2011 | Lee et al. |
| 2012/0295269 A1 | 11/2012 | Pourahmad et al. |
| 2013/0026051 A1 | 1/2013 | Nelson et al. |
| 2013/0098777 A1 | 4/2013 | Gaustad |
| 2013/0341186 A1* | 12/2013 | Hsu .................... G01N 27/3272 204/403.14 |
| 2014/0087375 A1* | 3/2014 | Kelley ................. C12Q 1/6837 435/287.2 |
| 2014/0194305 A1* | 7/2014 | Kayyem .............. C12Q 1/6825 506/18 |
| 2015/0140671 A1* | 5/2015 | Zhang ............... B01L 3/502707 436/69 |
| 2016/0084796 A1 | 3/2016 | Gasperino et al. |
| 2016/0091482 A1 | 3/2016 | Bauer-Espindola et al. |
| 2016/0107951 A1 | 4/2016 | Van Dam et al. |
| 2016/0235350 A1* | 8/2016 | Buse .................... A61B 5/1411 |
| 2016/0299138 A1* | 10/2016 | Almasri ............ B01L 3/502761 |
| 2016/0310948 A1 | 10/2016 | Nowakowski et al. |
| 2018/0251811 A1 | 9/2018 | Hughes et al. |
| 2019/0321819 A1 | 10/2019 | Arango et al. |

FOREIGN PATENT DOCUMENTS

| | | | |
|---|---|---|---|
| EP | 2703817 A1 | 3/2014 | |
| KR | 20110134017 A * | 12/2011 | |
| WO | WO 02/50534 A1 | 6/2002 | |
| WO | WO-2015003722 A1 * | 1/2015 | ........ B01L 3/502707 |
| WO | WO 2017/037695 A1 | 3/2017 | |

OTHER PUBLICATIONS

International Search Report and Written Opinion dated Feb. 18, 2020 issued in related PCT App. No. PCT/US2019/064060 (14 pages).

Srinivasan et al. "An integrated digital microfluidic lab-on-a-chip for clinical diagnostics on human physiological fluids," Lab on a Chip 4.4 (May 26, 2004): 310-315. Abstract, p. 311 col. 1, para 103; p. 312 col. 1 para 3; p. 312 col. 2 para 2; p. 313 col. 1 para 3; p. 313 col. 2 para 1-5; p. 314 col. 1 para 2-3; Figure 1; Figure 3; Figure 4; and Figure 5.

Chang et al. "Electrowetting on dielectric: a low voltage study on self-assembled monolayers and its wetting kinetics," 2004 International Conference on MEMS, NANO and Smart Systems (Aug. 25, 2004). Abstract; p. 1 col. 1 para 1-2; p. 1 col. 2 para 3; p. 2 col. 1 para 1; p. 6 col. 1 para 1; p. 6 col. 2 para 1.

Saeki et al. "Electrowetting on dielectrics (EWOD): reducing voltage requirements for microfluidics." Polym. Mater. Sci. Eng 85 (Aug. 2001): 12-13. p. 1 col. 1 para 104; p. 1 col. 1 para 9; p. 2 col. 1 para 1-2; Figure 1; and Figure 2.

Chung et al. "On-chip manipulation of objects using mobile oscillating bubbles," Journal of Micromechanics and Microengineering 18.12 (Nov. 19, 2008); 125024. Abstract, p. 2 col. 2 para 2; p. 3 col. 1 para 1; Figure 1; Figure 7.

European Search Report dated Jul. 20, 2022 issued in related European Patent App. No. 19892916.8 (10 pages).

Lin Hua et al., "Current Status of HbA1c Biosensors," vol. 17, No. 8, Jan. 1, 2017 (Jan. 1, 2017), p. 1798, XP55941163, DOI: 10.3390/s17081798; retrieved from the Internet: URL: Https://www.ncbi.nlm.gov/pmc/articles/PMC5579747/pdf/sensors-17-01798.pdf> *the whole document*.

European Search Report dated Jul. 27, 2022 issued in related European Patent App. No. 19893268.3 (9 pages).

Koo et al., "An inkjet-printed electrowetting valve for paper-fluidic sensors," Analyst, vol. 138, No. 17, Jun. 17, 2013 (Jun. 17, 2013), p. 4998, XP055456160, UK, ISSN: 0003-2654, DOI: 10.1039/c3an01114c *p. 5001; figure 1*.

Office Action in related Chinese patent application No. 201980079450.5, issued on Dec. 28, 2023 (25 pages).

* cited by examiner

SYSTEMS AND METHODS FOR A COMBINED STRIP DETECTION AND HEATING SYSTEM IN AN ELECTROCHEMICAL TEST STRIP

CROSS-REFERENCE TO RELATED APPLICATIONS

This application claims the benefit of U.S. provisional application No. 62/774,228 filed Dec. 2, 2018, the entirety of which is hereby incorporated by reference.

BACKGROUND

In many scenarios, doctors, consumers, and health professionals desire to test for various analytes. Although lab testing is readily available for users, such testing requires users to send away samples and results will not usually be ready quickly. Therefore, point of care (POC) testing systems are desirable. Some of the biggest factors affecting the sale and use of POC testing systems is the convenience, disposability, and ease of use provided by various systems. Therefore, systems that provide such factors are highly desirable.

BRIEF SUMMARY

In one embodiment, a system for testing for an analyte includes a test strip. The test strip includes a test strip detection conductor. The test strip includes a first flow path, the first flow path including a heating area, the test strip detection conductor in the heating area, the test strip detection conductor configured to be activated to heat a sample in the heating area. In one alternative, the test strip detection conductor is a gold resistive heating element. In another alternative, test strip further includes an e-gate, the e-gate in the first flow path, the e-gate separating the heating area from a detection area of the first flow path. In another alternative, the analyte is Hb A1C. Alternatively, the test strip further includes a second flow path, the second flow path including an interdigitated electrode for detecting hemoglobin. In another alternative, the system further includes a meter, which engages the test strip and is configured to detect the test strip via the test strip detection conductor. Alternatively, the meter configured to provide current to the test strip detection conductor and heat the sample in the heating area. Alternatively, meter is configured to open the e-gate when the sample has reached a necessary temperature. Alternatively, the meter is configured to open the e-gate after the sample has undergone necessary digestion. Alternatively, the meter is configured to provide current to the test strip detection conductor until the sample has reached a necessary temperature. Alternatively, the meter is configured to provide current to the test strip detection conductor until the sample has undergone necessary digestion.

In one embodiment, a method of heating a sample in a test strip includes providing a test strip and applying a sample to the test strip. The method further includes slowing the flow of the sample in a heating area of a first flow path, a test strip detection conductor in the heating area and heating the sample with the test strip detection conductor. In one alternative, the method includes detecting insertion of the test strip into a meter using the test strip detection conductor. Alternatively, the detecting including the meter providing a current to the test strip detection conductor. In another alternative, the test strip detection conductor is a gold resistive heating element. Alternatively, test strip further includes an e-gate, the e-gate in the first flow path, the e-gate separating the heating area from a detection area of the first flow path. In another alternative, the analyte is Hb A1C. Alternatively, the test strip further includes a second flow path, the second flow path including an interdigitated electrode for detecting hemoglobin. In another alternative, the method includes opening the e-gate when the sample has reached a necessary temperature. In another alternative, the method includes opening the e-gate after the sample has undergone necessary digestion.

In one embodiment, a system for testing for an analyte includes a test strip and a meter. The test strip includes a test strip detection conductor. The test strip further includes a first flow path, the first flow path including a heating area, the test strip detection conductor in the heating area. The test strip detection conductor is configured to be activated to heat a sample in the heating area. The test strip includes an e-gate, the e-gate in the first flow path, the e-gate separating the heating area from a detection area of the first flow path. The test strip further includes a second flow path, the second flow path including an interdigitated electrode for detecting hemoglobin. The meter is configured to provide current to the test strip detection conductor and heat the sample in the heating area. The meter is configured to open the e-gate when the sample has reached a necessary temperature.

DETAILED DESCRIPTION

Figure 1:
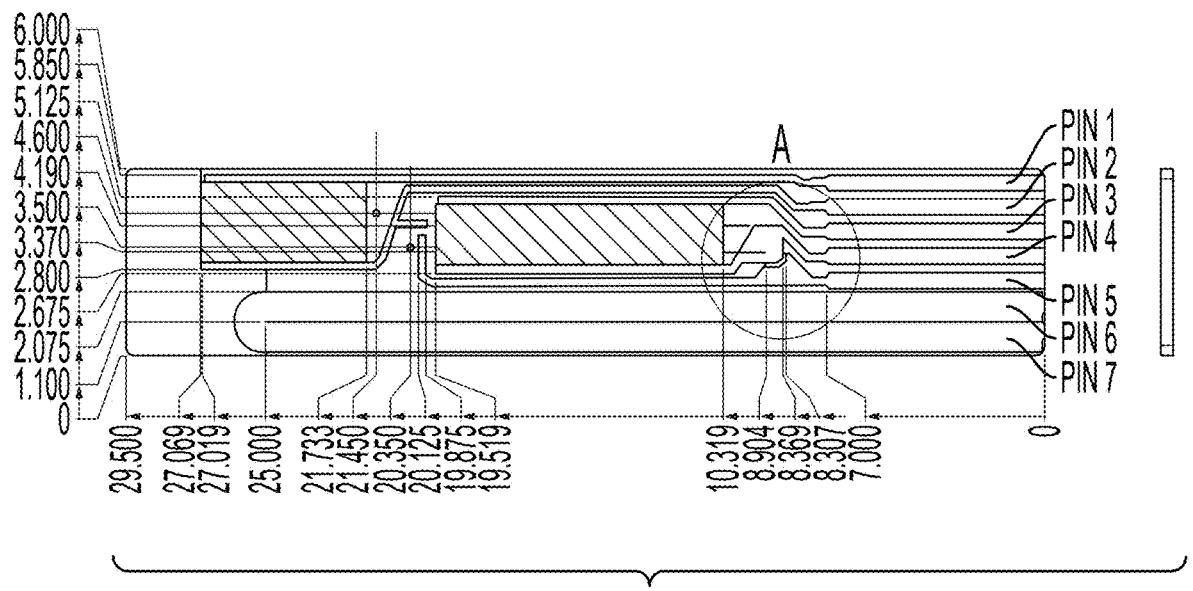
FIG. 1 shows a diagram of an embodiment of a combined strip detection and heating system in an electrochemical test strip.

Certain terminology is used herein for convenience only and is not to be taken as a limitation on the embodiments of the system and methods for combined strip detection and heating system in an electrochemical test strip. Essentially, the test strip includes a test strip detection system that also is used as a heating element for a sample. In many embodiments, the system tests for A1C and Hb. In many embodiments, the A1C sample must be heated in order to digest the sample and this is done via the combined strip detection and heating system in an electrochemical test strip.

In many embodiments, an important functional step of the assay is to heat the prepared A1C sample to digest the hemoglobin, prior to contact with the electrode area.

To meet cost and ease of use targets the biosensor strip is required to be a highly integrated, self-functional component of the overall product design. Similar to how an IC chip is to a PCB Assembly. After "analysis-for-integration," it was determined that the strip detect and the fill detect conductors on the biosensor strip could be "multi-purposed" for another design requirement; heating. The chemistry requires that the A1C lysed blood sample be heated to a temperature that significantly decreases the reaction time required. Therefore, in many embodiments, the conductive gold could be set up to be the resistive heating element needed for the chemistry requirements.

In many embodiments, the biosensor strip uses the strip detect conductor and the fill detect conductor to heat the sample to required temperature. The strip conductors are now applied with a voltage at intervals of time to generate a heat output (thermal watts) in order increase the chemistry temperature. Via an e-gate, the sample is typically held in the heating area. Alternative techniques are possible for holding the sample an area, including blister packs, mechanical gates, or dissolvable barriers.

Additionally, the system may include an e-gating feature in an electrochemical test strip (also referred to as an e-gated test strip or EGTS) for keeping the sample in a heating area. In many embodiments, an e-gated test strip includes a braking feature. By braking feature, it is meant to refer to a feature that stops of slows the flow of fluid in the test strip such that it does not completely advance into another area of the test strip. In many configurations, such braking features are implemented in a test strip utilizing microfluidics and/or capillary flow tubes. In many embodiments the braking feature is a hydrophobic glass bead dielectric that can be applied (screened) on top of the standard electric contacts on-strip. The thickness, wetting angle, feature geometry, potential applied, and channel height play important roles in the effectiveness of the design. In many embodiments, the braking feature is the ablated trough that is cut into the body of the base polymer film that the biosensor is fabricated from. The trough is a semicircular feature that has an approximate 1 to 1 ratio of diameter to fluid channel width. The depth and edge "sharpness" play a role in the reliability and longevity of the fluid to be held in place until the analyzer releases the fluid to the next stage. In many embodiments, the braking feature is a Self-Assembled Monolayer (SAM). This is a printed (screened or flood) process application that needs a temporary holding dam so that the fluid carrier can allow the features of the SAM to assemble properly and then remove the dam for the next component to be assembled. In many embodiments, the braking features do not need any external forces to function and stop the flow of fluid. Instead they function automatically based on current applied via electrodes from a meter. In alternatives, other braking techniques may be used for the e-gate that may be actuated by a current and do not require mechanical pieces.

In many embodiments, the combined strip detection and heating system test strip is used in the detection of hemoglobin and hemoglobin A1C such that a ratio of the two is calculated. As part of this assay, in many configurations, the flow of the lysed sample is controlled in order to provide a proper sequence in the system. In many configurations, the combined strip detection and heating system test strip is constructed as a multi-layer film strip biosensor. In many configurations, the biosensor has highly engineered film layers that control biosensor detection, electrical signals, fluid flow and heat. Important to this application is the control of fluid flow and location.

In some embodiment, the combined strip detection and heating system test strip integrates one of three differently fabricated, in-process braking features to provide a system that gives greatest reliability for control, near and long term. Of them, two of the three designs utilize an applied low voltage to the leading edge of the fluid to alter the wetting angle of the fluid so that the braking feature geometry is now misaligned and the capillary action of the wetted surfaces pulls or restarts the flow of the fluid into the measurement channel. The third braking feature takes advantage of the hydrophobic nature of a Self-Assembled Monolayer (SAM). The SAM has the ability to relax its hydrophobic characteristics due to an applied voltage and allow the fluid to restart into the measurement channel.

In many embodiments, the first braking feature is a hydrophobic glass bead dielectric that can be applied (screened) on top of the standard electric contacts on-strip. The thickness, wetting angle, feature geometry, potential applied, and channel height play important roles in the effectiveness of the design.

In many embodiments, the second braking feature design is the ablated trough that is cut into the body of the base polymer film that the biosensor is fabricated from. The trough is a semicircular feature that has an approximate 1 to 1 ratio of diameter to fluid channel width. The depth and edge 'sharpness" play a role in the reliability and longevity of the fluid to be held in place until the analyzer releases the fluid to the next stage.

In many embodiments, the third braking feature is the Self-Assembled Monolayer (SAM). This is a printed (screened or flood) process application that needs a temporary holding dam so that the fluid carrier can allow the features of the SAM to assemble properly and then remove the dam for the next component to be assembled.

Numerous advantages exist for the combined strip detection and heating system, including:
1.) Increased consumer use reliability; less components lead to less process failure
2.) Lower inventory requirements and manufacturing time.
3.) Lower product cost
4.) Lower shipping packaging and transit costs.
5.) The on-strip heating allows for reduced physical component tolerance stack up.
6.) It applies heat directly to the sample, improving consistency.

Figure 4:
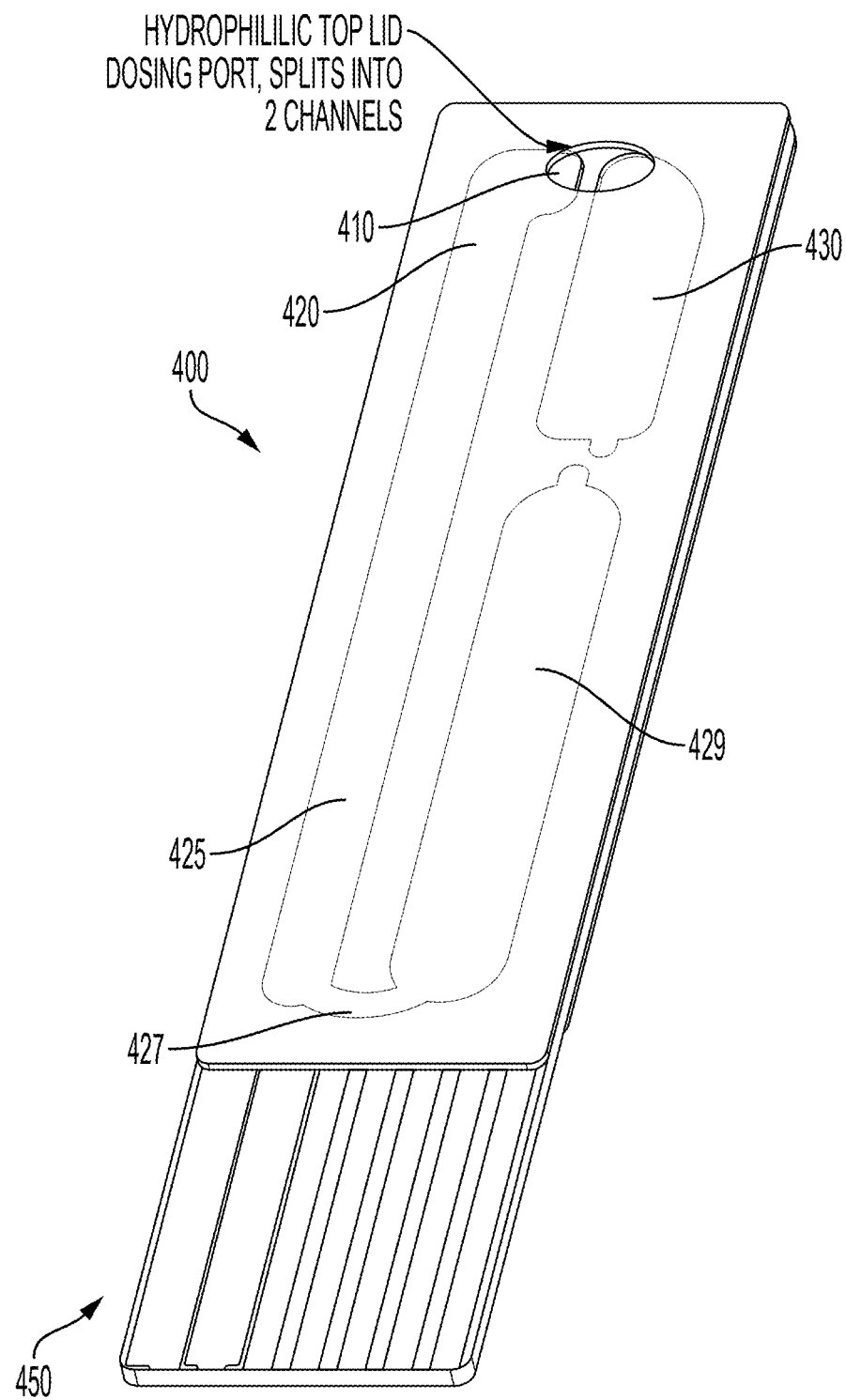
FIG. 4 shows another diagram of one embodiment of a combined strip detection and heating system in an electrochemical test strip.

FIG. 1 shows a diagram of an embodiment of a combined strip detection and heating system in an electrochemical test strip, with exemplary relative distances in millimeters. FIG. 4 shows a diagram of one embodiment of the combined strip detection and heating system test strip 400. In this diagram, the application port 410 is visible. Application port 410 is located in a hydrophobic cover for the strip. Also visible are the two flow channels of the device, A1C channel 420 and Hb channel 430. In A1C channel 420 there two primary areas, heating area 425 and detection area 429 which are separated by an e-gate 427. In the heating area, the sample is heated via the combined strip detection and heating system. Also, the electrode leads 450 are visible. This setup is used because the Hb channel does not require heating/digestion, so the sample can proceed immediately to the detection area, whereas in the A1C channel 420, digestion is first necessary. The trace of the various circuitry is not visible in this configuration.

In many embodiments, in heating area 425, the sample is heated and digested. This may occur according to a variety of techniques; however, it is important to prevent the advance of the sample beyond. This is the purpose of the e-gate.

Figure 2:
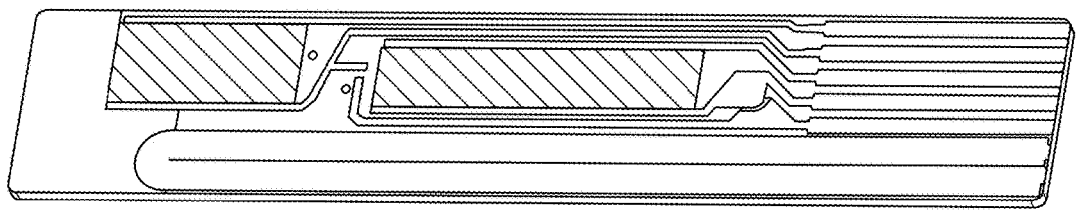
FIG. 2 shows a perspective view of a diagram of the combined strip detection and heating system in an electrochemical test strip of FIG. 1.

Table 1 below shows an explanation of the process flow for embodiments of the combined strip detection and heating system test strip. Typically, circuitry/logic in a meter controls the operation of the test strip, however, such control circuitry/logic may be resident in any device that engages the test strip. As shown in the table below and FIGS. 1 and 2, the electrode and pin arrangement are shown. When the test strip is first introduced into the meter and the meter is activated, the system detects the strip via pin 6 and 7. This is event 1. These pins, 6 and 7, are part of a u-shaped trace. Pin 5 and pin 6 detect that heating area 425 has been filled. This is event 2. Pin 1 and pin 2 are provided for use in measuring the hemoglobin in the sample provided. This is event 3. Subsequently, in event 4, pin 6 and pin 7 cooperate to heat the sample for the A1C side of the test in event 4. Once the sample is sufficiently heated, the pins 4, 5, and 6 are used to release the e-gate, in event 5. In event 6, Pin 2 and 5 are used to detect a fill of the A1C detection area 429. Subsequently, in event 7, pin 3 and pin 4 provide for the detection and measurement of A1C, providing a counter electrode and a working electrode.

1130, 1160 in the cover that is laid over the spacer. The device includes a digestion finger 1110 and digestion channel 1120, where the sample may be heated such that digestion can occur. In alternative embodiments, other chemical procedures may occur in this channel. A1C finger 1140 leads to electrode area 1040 where electrochemical testing may occur. The A1C channel 1150 lead to the area over electrode area 1040. Additionally, including is a channel that does not require digestion, channel 1170 over electrode 1030. This channel 1170 includes a vent 1160 in the cover. In many embodiments this channel is a hemoglobin channel.

Therefore, in many embodiments, a test strip is provided that has a single stage electrochemical detection system and a dual stage electrochemical detection system. A single port leads to both electrochemical detection systems and the flow paths for each. On the single stage electrochemical detection

| | | Signal | | | | | | |
|---|---|---|---|---|---|---|---|---|
| PIN # | CHEMISTRY | Event 1 | Event 2 | Event 3 | Event 4 | Event 5 | Event 6 | Event 7 |
| 1 | Hb | | | Counter | | | | |
| 2 | Hb | | | Working | | | Fill A1C | |
| 3 | A1C | | | | | | | Counter |
| 4 | A1C | | | | | Release E-Gate | | Working |
| 5 | A1C | | Heat Channel Fill | | | Release E-Gate | Fill A1C | |
| 6 | A1C | Strip Detect | Heat Channel Fill | | Heat | Release E-Gate | | |
| 7 | | Strip Detect | | | Heat | | | |

Figure 3A:
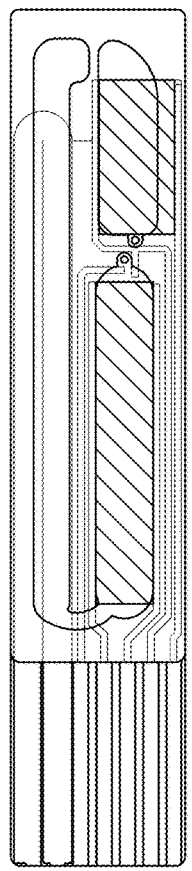
FIG. 3A-3C show additional diagrams of the e-gated combined strip detection and heating system in an electrochemical test strip of FIG. 1.
Figure 3B:
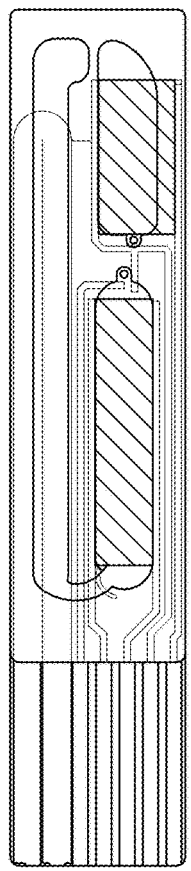
Figure 3C:
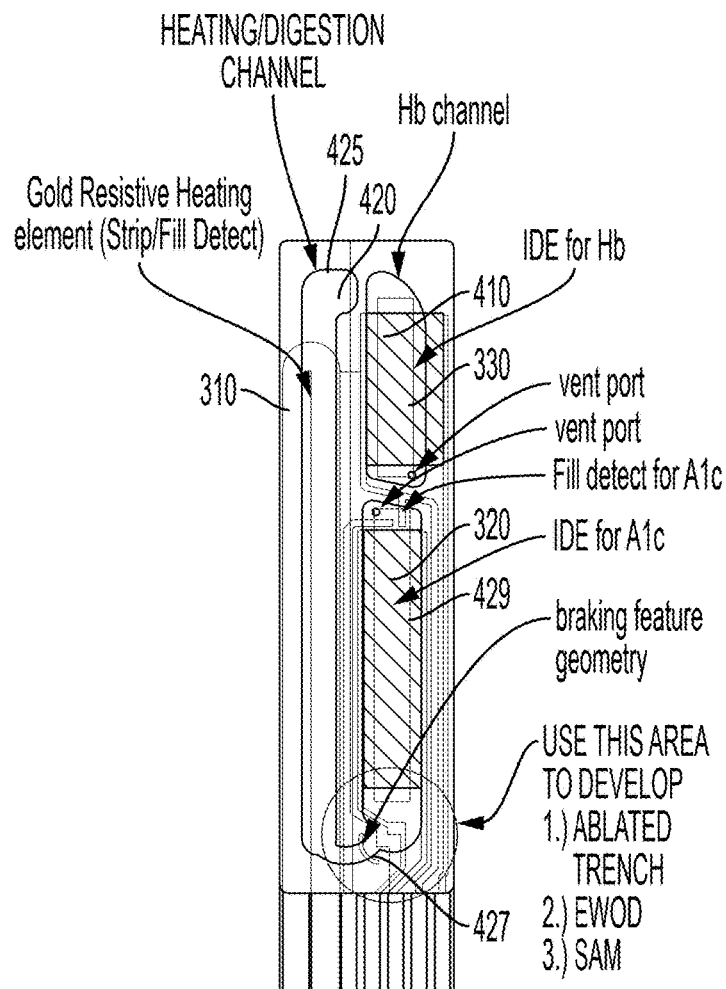

FIG. 3A-3C provide more detail concerning the system. As shown in 3C, a heating/digestion channel or heating area 425 on the AIC channel 420 side is provided. Under this channel is the gold resistive heating element 310 that also provides for the detection of the insertion of the strip. This is one possible embodiment of the combined strip detection and heating system. Other resistive elements are possible, that will provide heat and detection of insertion. One of three possible techniques for e-gating is used at e-gate 427. Subsequently, in detection area 429 an interdigitated electrode 320 for A1C is located that allows for the measurement of A1C. On the Hb channel, a Hb interdigitated electrode 330 is provided for the measurement of hemoglobin.

Figure 5:
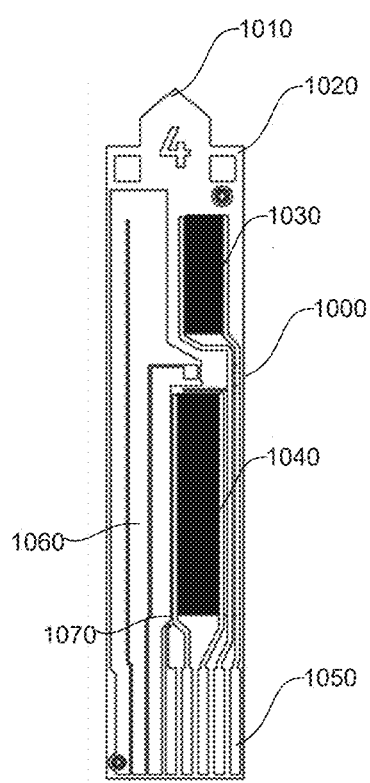
FIG. 5 shows another embodiment of a test strip for an ICA (Integrated Consumable Assay)

FIG. 5 shows another embodiment of a test strip for an ICA, specifically the substrate piece. This test strip 1000 is specifically designed to include a piercing end 1010. The strip also includes a stop 1020 to prevent the strip from advancing too far. In this embodiment, the piercing end 1010 is designed to pierce a reservoir that holds reactants or lysing agents (or some other material for interacting with the sample). Additionally, in this view, electrode areas 1030, 1040 are shown. In many embodiments these are interdigitated electrodes but other configurations are possible. Leads 1050 interact with a meter in order to power the strip to detect the analyte of interest. In alternatives, the strip may still include the piercing end 1010, however may be an optical strip. Electrodes 1060 provides for a hearing element, that may heat a sample by powering the electrodes. Additionally, at finger 1140 shown in FIG. 6, the two leads located at 1070 provide electrical energy to electrically active the e-gate located at this area.

Figure 6:
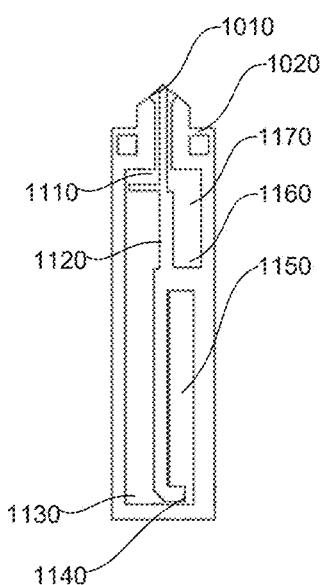
FIG. 6 shows the flow areas for the test strip of FIG. 5.

FIG. 6 shows the flow path etching that is laid over the substrate piece of FIG. 6. Additionally, a cover, not show, is laid over the substrate. Similarly, the device includes pierce point 1010 that aligns with the pierce point 1010 on the substrate. The strip also includes a stop 1020 to prevent the strip from advancing too far. Typically the channels of the device rely on capillary type flow action and include vents system side, the flow path leads to a working electrode and counter electrode arrangement, whereby a level of a first analyte may be detected. One the dual stage electrochemical detection system side, the flow path first leads to a heating/digestion area. This area is heated by the combined strip detection and heating system. This area is separated from a detection area via an e-gate. The e-gate may automatically be opened and triggered by the meter (or other electrical source) connected to the test strip. Once the sample is heated/digested sufficiently, the gate is opened and the sample proceeds to the detection area. In many embodiments the single stage electrochemical detection system is for Hb. In many embodiments the dual stage electrochemical detection system is for A1C.

In many embodiments, a meter associated with the combined strip detection and heating system test strip includes logic for running the test, including, but not limited to, logic for detecting when/whether the strip is inserted (performed using the combined strip detection and heating system); logic for beginning the testing; logic for determining when the heating area is filled; logic for activating the heating element in the heating area (using the combined strip detection and heating system); logic for releasing the e-gate when the sample is sufficiently digested/heated; logic for determining when the A1C testing area is full; logic for activating the electrodes for determining A1C levels; logic for determining when the Hb testing area is full; logic for activating the electrodes for determining A1C levels; logic for outputting a result (in many scenarios including the ratio of Hb/A1C). In many scenarios, this logic includes activating and deactivating various electrodes/leads by providing current or voltage to the pins as discussed above.

In many embodiments, parts of the system are provided in devices including microprocessors. Various embodiments of the systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of the systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

In sum, with respect to the description herein, numerous specific details are provided, such as examples of components and/or methods, to provide a thorough teaching and understanding of embodiments of the present invention. One skilled in the relevant art will recognize, however, that an embodiment can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Similarly, embodiments can be implemented in many forms, and based on the disclosure and teachings provided herein, a person of ordinary skill in the art will appreciate other ways and/or methods to implement an equivalent. Reference throughout this specification to "one embodiment", "an embodiment", or "a specific embodiment" means that a particular feature, structure, or characteristic described in connection with the embodiment is included in at least one embodiment and not necessarily in all embodiments. Thus, respective appearances of the phrases "in one embodiment", "in an embodiment", or "in a specific embodiment" in various places throughout this specification are not necessarily referring to the same embodiment.

Furthermore, the particular features, structures, or characteristics of any specific embodiment may be combined in any suitable manner with one or more other embodiments. It is to be understood that other variations and modifications of the embodiments described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as otherwise operable in certain cases, as is useful in accordance with a particular application.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments, including what is described in the Abstract and the Summary and the overview paragraphs, are not intended to be exhaustive or to limit the disclosed system, apparatuses, methods, compositions of matter or other disclosed subject matter to the precise forms disclosed herein. While specific embodiments of, and examples for, the disclosed system, apparatuses, methods, compositions of matter or other disclosed subject matter are described herein for teaching-by-illustration purposes only, various equivalent modifications are possible within the spirit and scope of the disclosed system, apparatuses, methods, compositions of matter or other disclosed subject matter, as those skilled in the relevant art will recognize and appreciate. As indicated, these modifications may be made in light of the foregoing description of illustrated embodiments and are to be included within the true spirit and scope of the disclosure herein provided.

What is claimed as new and desired to be protected by Letters Patent of the United States is:

1. A system for testing for an analyte, the system comprising:
    a test strip including:
        a test strip detection conductor, the test strip detection conductor configured and arranged to provide a signal indicating a heating area has been filled when a first electrical contact and a second electrical contact are powered by a meter;
        a first flow path, the first flow path including the heating area, the test strip detection conductor in the heating area, the test strip detection conductor configured to be activated to heat a sample in the heating area when the second electrical contact and a third electrical contact are powered by the meter; wherein test strip further includes an e-gate, the e-gate in the first flow path, the e-gate separating the heating area from a detection area of the first flow path;
        a second flow path;
        an application port in communication with the first flow path and the second flow path, such that both flow paths may receive the sample, wherein the first flow path has a u-shape, such that the first flow path wraps around the test strip, the e-gate at a base point of the u-shape.

2. The system of claim 1, wherein the test strip detection conductor is a gold resistive heating element.

3. The system of claim 2, wherein the analyte is Hb A1C.

4. The system of claim 3, wherein the second flow path includes an interdigitated electrode for detecting hemoglobin.

5. The system of claim 4, wherein the meter engages the test strip and is configured to detect the test strip via the test strip detection conductor.

6. The system of claim 5, wherein the meter is configured to provide current to the test strip detection conductor and heat the sample in the heating area.

7. The system of claim 6, wherein the meter is configured to open the e-gate when the sample has reached a necessary temperature.

8. The system of claim 6, wherein the meter is configured to open the e-gate after the sample has undergone necessary digestion.

9. The system of claim 6, wherein the meter is configured to provide current to the test strip detection conductor until the sample has reached a necessary temperature.

10. The system of claim 6, wherein the meter is configured to provide current to the test strip detection conductor until the sample has undergone necessary digestion.

11. The system of claim 1, wherein the test strip detection conductor is in communication with the meter and the combination of the meter and the test strip detection conductor create the signal when the heating area is filled, the signal indicative of a fill state.

12. The system of claim 1, wherein the first electrical contact is a first pin, the second electrical contact is a second pin, and the third electrical contact is a third pin.

13. A system for testing for an analyte, the system comprising:
   a test strip including:
      a test strip detection conductor, the test strip detection conductor configured and arranged to provide a signal indicating a heating area has been filled;
      a first flow path, the first flow path including the heating area, the test strip detection conductor in the heating area, the test strip detection conductor configured to be activated to heat a sample in the heating area; wherein the test strip includes an e-gate, the e-gate in the first flow path, the e-gate separating the heating area from a detection area of the first flow path and the test strip further includes a second flow path, the second flow path including an interdigitated electrode for detecting hemoglobin;
   a meter configured to provide current to the test strip detection conductor and heat the sample in the heating area; wherein the meter is configured to open the e-gate when the sample has reached a necessary temperature wherein when a first electrical contact and a second electrical contact are powered by the meter the signal indicating the heating area has been filled is activated; when the second electrical contact and a third electrical contact are powered by the meter the test strip detection conductor is activated;
   an application port in communication with the first flow path and the second flow path, such that both the flow paths may receive the sample, wherein the first flow path has a u-shape, such that the first flow path wraps around the test strip, the e-gate at a base point of the u-shape.

14. The system of claim 13, wherein the test strip detection conductor is in communication with the meter and the combination of the meter and the test strip detection conductor create the signal when the heating area is filled, the signal indicative of a fill state.

15. They system of claim 13, wherein the first electrical contact is a first pin, the second electrical contact is a second pin, and the third electrical contact is a third pin.

* * * * *